(12) United States Patent
Falabella et al.

(10) Patent No.: US 7,938,011 B1
(45) Date of Patent: May 10, 2011

(54) HIGH SHOCK TEST APPARATUS

(75) Inventors: David Falabella, Merritt Island, FL (US); Gary A. Simpson, Apopka, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 415 days.

(21) Appl. No.: 12/130,248

(22) Filed: May 30, 2008

(51) Int. Cl.
*G01N 29/00* (2006.01)
(52) U.S. Cl. .......................................... 73/668; 73/663
(58) Field of Classification Search ............... 73/668, 73/663
See application file for complete search history.

(56) References Cited

U.S. PATENT DOCUMENTS

| | | | | |
|---|---|---|---|---|
| 3,585,350 A | * | 6/1971 | Voytko | 219/121.63 |
| 4,314,479 A | * | 2/1982 | Spijkerman | 73/643 |
| 5,471,865 A | * | 12/1995 | Michalewski et al. | 72/430 |
| 6,453,790 B1 | * | 9/2002 | Cesulka et al. | 89/1.11 |
| 7,530,737 B2 | * | 5/2009 | Thompson et al. | 374/136 |

* cited by examiner

*Primary Examiner* — Jacques M Saint Surin
(74) *Attorney, Agent, or Firm* — Jeffrey D. Myers; Samantha A. Updegraff; Timothy D. Stanley

(57) ABSTRACT

A testing apparatus and method comprising providing a platform for a unit under test, charging a capacitor bank with a charging system, with a switching and power control system generating multiple pulses per cycle from energy from the capacitor bank, and with an electromagnetic force generator receiving pulses from the switching and power control system and directing force at the platform.

24 Claims, 3 Drawing Sheets

HIGH SHOCK TEST APPARATUS

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to apparatuses and environments for testing devices subjected to high levels of shock.

2. Description of Related Art

Currently, there does not exist a means of replicating the shock environment produced during a Hardened and Deeply Buried Targets (HDBT) penetration event. The magnitude, duration, and multiple +/- shocks encountered during these events are currently only replicated through full scale sled tests that can cost hundreds of thousands of dollars per test. This results in either very expensive weapon system development cost due to multiple tests, or low/no confidence in component reliability due to limited testing. This apparatus may also be used to produce high shocks for the testing of other items that are subjected to large shocks such as aircraft flight data recorders, The present invention substantially replicates the HDBT penetration environment with a piece of lab suitable equipment that reduces test costs up to two orders of magnitude. The invention uses the high power storage and control methods utilized in high power rail/coil gun and pulsed laser applications to electromagnetically generate the multi-direction shock pulses representative of HDBT penetrations.

BRIEF SUMMARY OF THE INVENTION

The present invention is of a testing apparatus and method comprising: providing a platform for a unit under test; charging a capacitor bank with a charging system; with a switching and power control system generating multiple pulses per cycle from energy from the capacitor bank; and with an electromagnetic force generator receiving pulses from the switching and power control system and directing force at the platform. In the preferred embodiment, the invention delivers (assuming no losses) at least approximately 100 J of energy per cycle to the unit under test, and completes a cycle in approximately 20 to 2000 microseconds. The unit under test is preferably one or more of fuzes, projectile components, scientific probes, down-hole well components, and aircraft black boxes. The invention generates conditions to the unit under test simulating a Hardened and Deeply Buried Targets penetration by a projectile or other extreme, multiple shock environment.

The invention is additionally of an apparatus and method for testing devices by simulating an impact event's effects on a unit under test, comprising: charging a capacitor bank with a charging system; with a switching and power control system generating multiple pulses per cycle from energy from the capacitor bank; and with an electromagnetic force generator receiving pulses from the switching and power control system and directing force at the unit under test. In the preferred embodiment, the invention consumes at least approximately 10 KJ of energy per cycle and completes a cycle in approximately 20 to 2000 microseconds. The unit under test is preferably one or more of fuzes, projectile components, scientific probes, down-hole well components, and aircraft black boxes. The invention generates conditions to the unit under test simulating a Hardened and Deeply Buried Targets penetration by a projectile.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention provides an apparatus to replicate multiple, very high shocks similar to those seen by penetrating and gun launched weapons or instrumentation utilizing the high power storage and manipulation technologies used in rail/coil guns and high power laser/microwave systems, and rail or coil gun electromagnetic (EM) force generation techniques. The compelling argument for such a device is to be able to perform the majority of the testing for a HDBT weapon component for tens of thousands of dollars, as opposed to the hundreds of thousands of dollars required for full scale sled testing. Other devices subjected to high-stress environments can be similarly tested.

The invention is viable from an energy storage/transfer standpoint, requiring about 10 KJ of energy per cycle.

Figure 1:
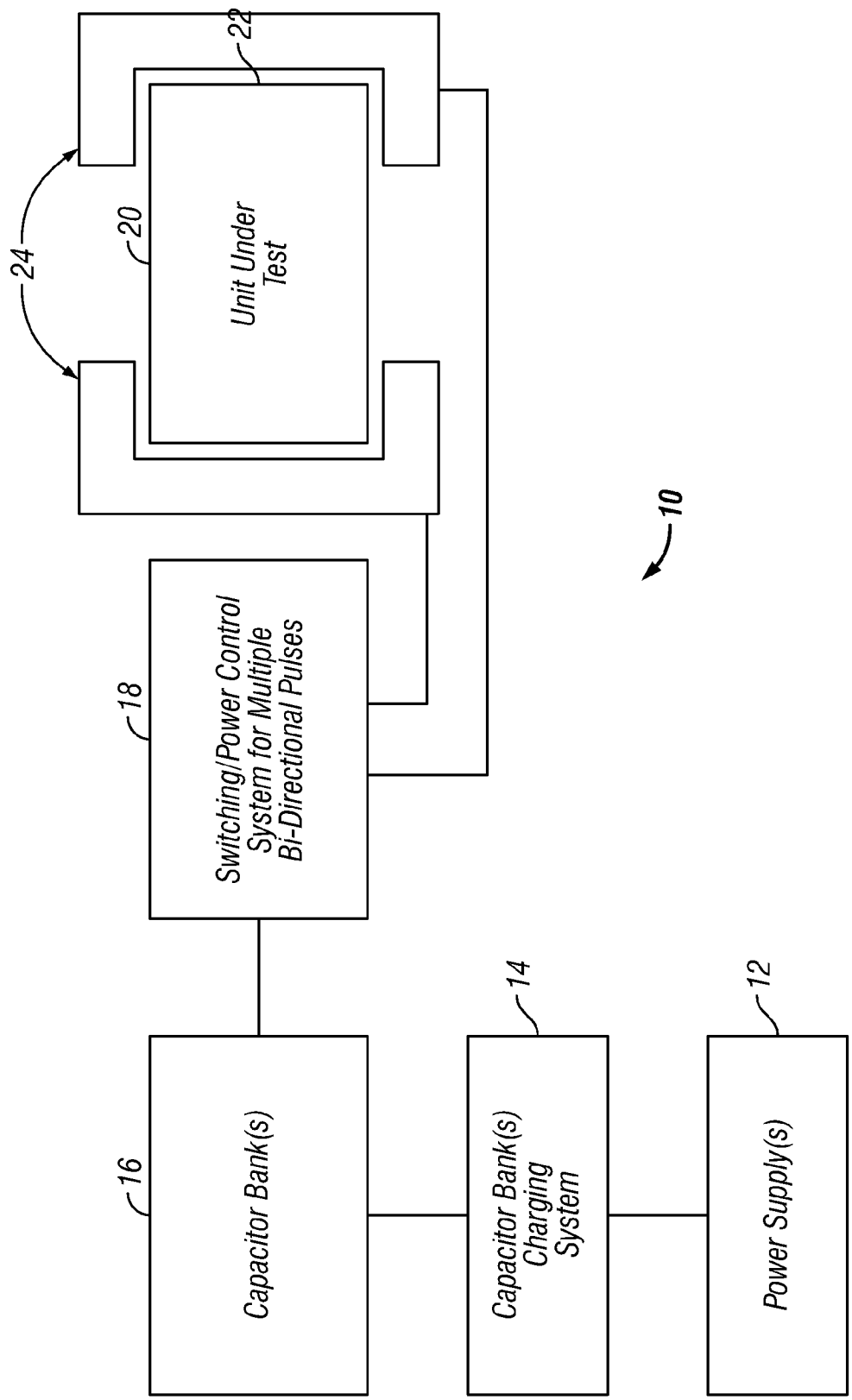
FIG. 1 is a schematic diagram of the apparatus of the invention.

FIG. 1 schematically illustrates the preferred apparatus 10 of the invention, comprising power supply(ies) 12, capacitor bank(s) charging systems 14, capacitor bank(s) 16, switching/power control system for multiple pulses 18, and EM force generator(s) 20 (single or multi-axis) acting on one or more units under test held by platform or platforms 22 and acting via single or multi-arm EM force generating devices 24.

Figure 2:
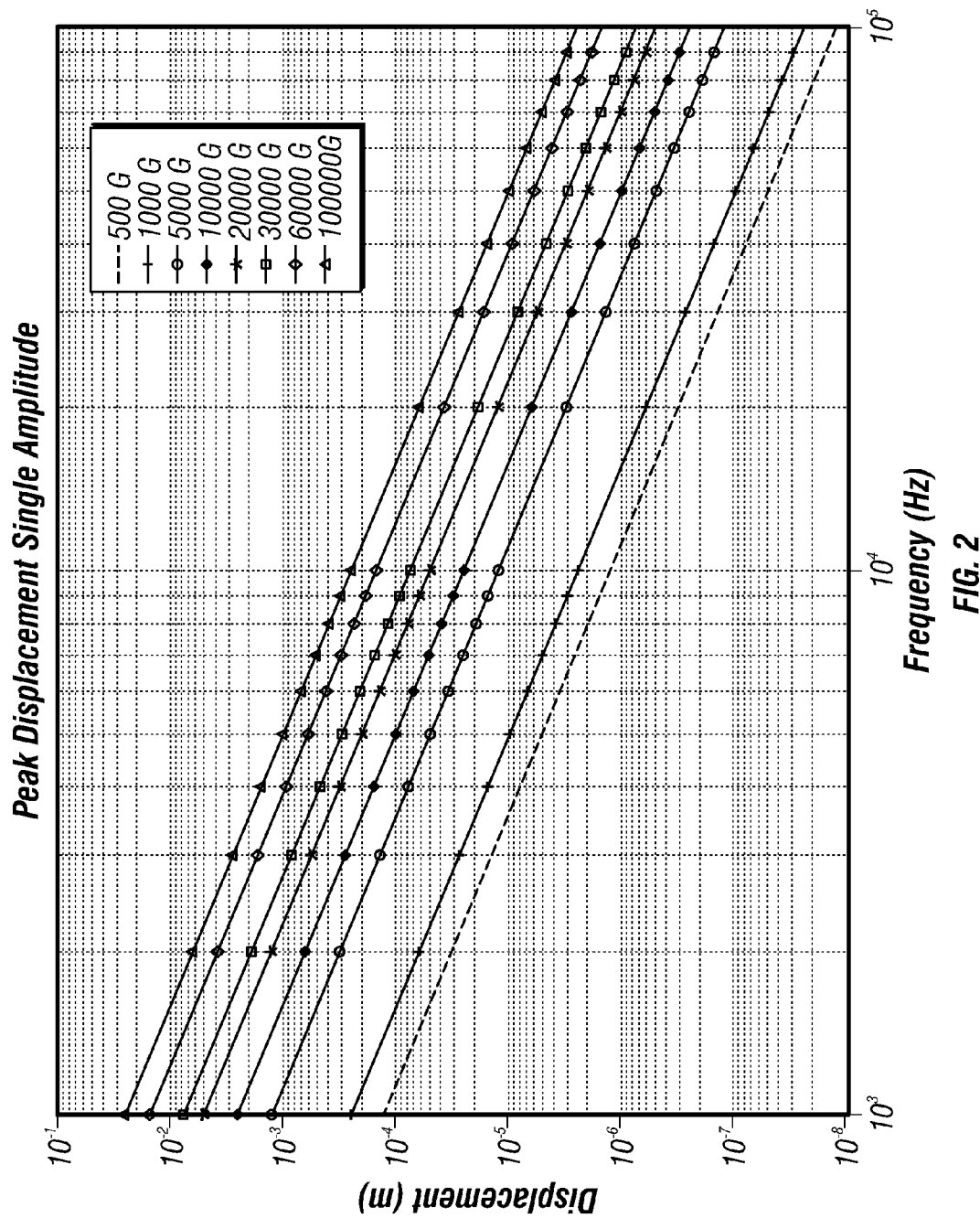
FIG. 2 is a graph of the displacements required for replication of HDBT environments.
Figure 3:
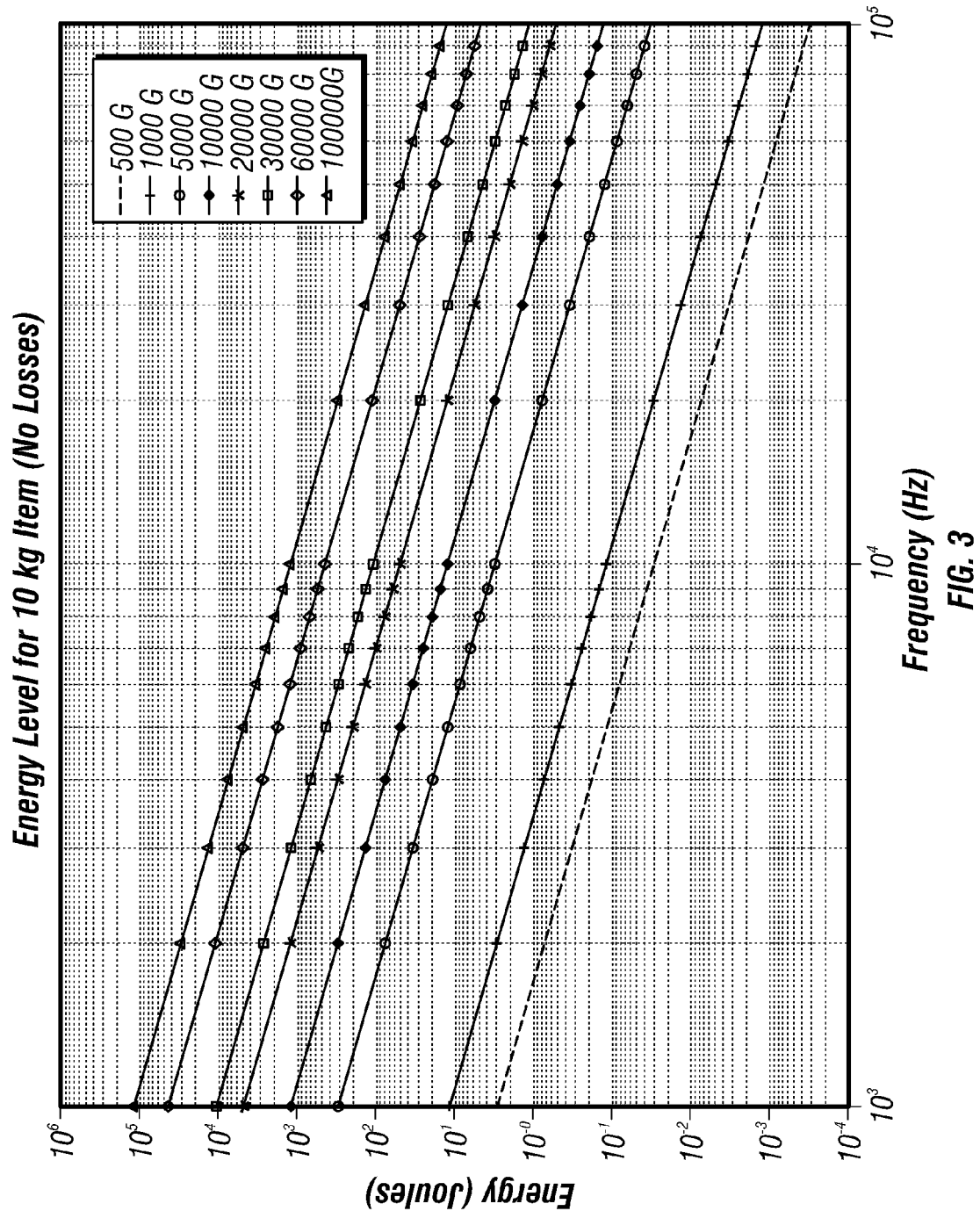
FIG. 3 is a graph of the energy/cycle required for replication of HDBT environments.

FIG. 2 is a graph of the displacements required for replication of HDBT environments, and FIG. 3 is a graph of the energy/cycle required for replication of HDBT environments. The present invention meets these requirements.

The invention is primarily useful in testing weapon or other application systems and components that are subjected to multiple high shocks such as HDBT fuzes, gun launch/impact items, earth/planetary science probes, down-hole oil/gas well components, and commercial components that must survive crashes, such as aircraft "black boxes".

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A testing apparatus comprising:
   a platform for a unit under test;
   a capacitor bank;
   a charging system charging said capacitor bank;
   a switching and power control system generating multiple pulses per cycle from energy from said capacitor bank; and
   an electromagnetic force generator receiving pulses from said switching and power control system and directing force at said platform; and
   wherein said apparatus generates conditions to the unit under test simulating a multi-directional shock pulse.

2. The apparatus of claim 1 wherein said apparatus consumes at least approximately 10 KJ of energy per cycle.

3. The apparatus of claim 1 wherein said apparatus completes a cycle in approximately 20 to 2000 microseconds.

4. The apparatus of claim 1 wherein the unit under test comprises one or more of the group consisting of fuzes, projectile components, scientific probes, down-hole well components, and aircraft black boxes.

5. The apparatus of claim 1 wherein said apparatus generates conditions to the unit under test simulating a Hardened and Deeply Buried Targets penetration by a projectile.

6. An apparatus for testing devices by simulating an impact event's effects on a unit under test, said apparatus comprising:
   a capacitor bank;
   a charging system charging said capacitor bank;
   a switching and power control system generating multiple pulses per cycle from energy from said capacitor bank; and
   an electromagnetic force generator receiving pulses from said switching and power control system and directing force at the unit under test; and
   said apparatus generates conditions to the unit under test simulating multi-directional shock pulse.

7. The apparatus of claim 6 wherein said apparatus consumes at least approximately 10 KJ of energy per cycle.

8. The apparatus of claim 6 wherein said apparatus completes a cycle in approximately 20 to 2000 microseconds.

9. The apparatus of claim 6 wherein the unit under test comprises one or more of the group consisting of fuzes, projectile components, scientific probes, down-hole well components, and aircraft black boxes.

10. The apparatus of claim 6 wherein said apparatus generates conditions to the unit under test simulating a Hardened and Deeply Buried Targets penetration by a projectile.

11. A testing method comprising the steps of:
    providing a platform for a unit under test;
    charging a capacitor bank with a charging system;
    with a switching and power control system generating multiple pulses per cycle from energy from the capacitor bank;
    with an electromagnetic force generator receiving pulses from the switching and power control system and directing force at the platform; and
    generating conditions to the unit under test simulating a multi-directional shock pulse.

12. The method of claim 11 wherein the method consumes at least approximately 10 KJ of energy per cycle.

13. The method of claim 11 wherein the method completes a cycle in approximately 20 to 2000 microseconds.

14. The method of claim 11 wherein the unit under test comprises one or more of the group consisting of fuzes, projectile components, scientific probes, down-hole well components, and aircraft black boxes.

15. The method of claim 11 wherein the method generates conditions to the unit under test simulating a Hardened and Deeply Buried Targets penetration by a projectile.

16. A method for testing devices by simulating an impact event's effects on a unit under test, the method comprising:
    charging a capacitor bank with a charging system;
    with a switching and power control system generating multiple pulses per cycle from energy from the capacitor bank;
    with an electromagnetic force generator receiving pulses from the switching and power control system and directing force at the unit under test; and
    generating conditions to the unit under test simulating a multi-directional shock pulse.

17. The method of claim 16 wherein the method consumes at least approximately 10 KJ of energy per cycle.

18. The method of claim 16 wherein the method completes a cycle in approximately 20 to 2000 microseconds.

19. The method of claim 16 wherein the unit under test comprises one or more of the group consisting of fuzes, projectile components, scientific probes, down-hole well components, and aircraft black boxes.

20. The method of claim 16 wherein the method generates conditions to the unit under test simulating a Hardened and Deeply Buried Targets penetration by a projectile.

21. The apparatus of claim 1 wherein the multi-directional shock pulse is representative of a projectile penetration.

22. The apparatus of claim 6 wherein the multi-directional shock pulse is representative of a projectile penetration.

23. The method of claim 11 wherein the multi-directional shock pulse is representative of a projectile penetration.

24. The method of claim 16 wherein the multi-directional shock pulse is representative of a projectile penetration.

* * * * *